US008071356B2

(12) United States Patent
Ammendola et al.

(10) Patent No.: US 8,071,356 B2
(45) Date of Patent: Dec. 6, 2011

(54) SALMONELLA ENTERICA STRAINS OF REDUCED PATHOGENICITY, METHOD FOR THEIR PREPARATION AND USES THEREOF

(75) Inventors: Serena Ammendola, Rome (IT); Andrea Battistoni, Rome (IT); Paolo Pasquali, Rome (IT)

(73) Assignees: Universita Degli Studi Di Roma "Tor Vergata", Rome (IT); I Stituto Superiore Di Sanita, Rome (IT)

( * ) Notice: Subject to any disclaimer, the term of this patent is extended or adjusted under 35 U.S.C. 154(b) by 0 days.

(21) Appl. No.: 12/305,609

(22) PCT Filed: Jun. 8, 2007

(86) PCT No.: PCT/IT2007/000410
§ 371 (c)(1),
(2), (4) Date: Jan. 22, 2009

(87) PCT Pub. No.: WO2007/148363
PCT Pub. Date: Dec. 27, 2007

(65) Prior Publication Data
US 2009/0175913 A1    Jul. 9, 2009

(30) Foreign Application Priority Data
Jun. 21, 2006  (IT) .............................. RM2006A0328

(51) Int. Cl.
*C12N 1/20* (2006.01)
*A61K 45/00* (2006.01)
*A61K 39/112* (2006.01)
(52) U.S. Cl. ................ 435/252.3; 424/258.1; 424/282.1
(58) Field of Classification Search ............... 424/258.1, 424/282.1; 435/252.3
See application file for complete search history.

(56) References Cited

U.S. PATENT DOCUMENTS
6,248,329 B1 * 6/2001 Chandrashekar et al. . 424/191.1

OTHER PUBLICATIONS

Campoy et al 2002 vol. 70 No. 8 pp. 4721-4725.*
Ellis (Chapter 29 of Vaccines, Plotkin, et al. (eds) WB Saunders, Philadelphia, 1998, especially p. 571, paragraph 2).*
2nd Annual ASM conference Salmonella: From Pathogenesis to therapeutics Sep. 2006, B17 Ammendola et al, Role of Zinc in the Host-Salmonella interaction pp. 1-105.*
Dec. 27, 2007, International Search Report in PCT/IT2007/000410.
Written Opinion in PCT/IT2007/000410
Aug. 1, 2002, Campoy, Susana et al: "Role o f the high-affinity zinc uptake znuABC system in *Salmonella enterica* serovar typhimurium virulence," *Infection and Immunity*, vol. 70, No. 8, Aug. 2002, pp. 4721-4725; XP002453141; ISSN: 0019-9567.
Apr. 1, 2003, Garrido Melena et al: "The high-affinity zinc-uptake system znuACB is under control of the iron-uptake regulator (fur) gene in the animal pathogen *Pasteurella multocida*," *FEMS Microbiology Letters*, vol. 221, No. 1, Apr. 1, 2003 (Apr. 11, 2003), pp. 31-37; XP002453142; ISSN: 0378-1097.
Jun. 1, 1998, Patzer Silkeiet al: "The ZnuABC high-affinity zinc uptake system and its regulator Zurin *Escheri chiacoli*," *Molecular Microbiology*, vol. 28, No. 6, Jun. 1998, pp. 1199-1210; XP002453143; ISSN: 0950-382X.
Oct. 1, 1999, Lewis DA et al: "Identificiation of the znuA-encoded periplasmic zinc transport protein of *Haemophilus ducreyi*," *Infection and Immunity*, American Society for Microbiology, Washington, US, vol. 67, No. 10, Oct. 1999, pp. 5060-5068; XP002253820; ISSN: 0019-9567.
Sep. 1, 2004, Kim Suk et al: "Zinc uptake system (znuA locus) of Bruce1 1 a abortus is essential for intracellular survival and virulence in mice," *Journal of Veterinary Medical Science*, vol. 66, No. 9, Sep. 2004, pp. 1059-1063, XP002453144 ISSN: 0916-7250.
Jul. 1, 2006, Yang Xinghong et al: "Deletion of znuA virulence factor attenuates *Brucella abortus* and confers protection against wild-type challenge," *Infection and Immunity* Jul. 2006, vol. 74, No. 7, pp. 3874-3879, XP002453145; ISSN: 0019-9567.

* cited by examiner

*Primary Examiner* — Gary Nickol
*Assistant Examiner* — Nina Archie
(74) *Attorney, Agent, or Firm* — Arent Fox, LLP

(57) ABSTRACT

The invention concerns novel *Salmonella enterica* attenuated strains, characterized in that they are inactivated at the level of the znuABC operon through mutation in at least one of the znuA, znuB, znuC genes of such operon, for uses in medical or veterinary fields as vaccines.

15 Claims, 7 Drawing Sheets

A

B

C

SALMONELLA ENTERICA STRAINS OF REDUCED PATHOGENICITY, METHOD FOR THEIR PREPARATION AND USES THEREOF

SEQUENCE LISTING

The instant application contains a Sequence Listing which has been submitted via EFS-Web and is hereby incorporated by reference in its entirety. Said ASCII copy is named 12305609.txt.

This application is a PCT national stage entry of PCT/IT2007/000410 filed Jun. 8, 2007, published Dec. 27, 2007 as WO 2007/148363, and claims Paris priority to Italian application RM2006A00328 filed Jun. 21, 2006.

The present invention relates with new strains of *Salmonella enterica* with reduced pathogenicity, the method to obtain such attenuated strains, and their use as vaccine strains or carriers to express heterologous protective antigens in veterinary or medical field against infections due to *Salmonella* sp or other pathogens.

Prevention of infectious diseases in farm animals is an important task in zootechny due to both the economic consequences of infectious diseases outbreaks in animals in intensive rearing, and the possible implications of such diseases on health of the consumers. The use of effective vaccines against the major zoonotic agents is highly recommended in order to safeguard public health since, further lowering bacterial food stuff contamination risk, it limits the use of therapy based on antibiotics.

Among the major zoonotic agents, there are bacteria belonging to genus *Salmonella* sp *enterica*. These are able to colonize intestine of several species, to contaminate food and feedstuff and to induce in a broad range of pathological pictures, ranging from acute enteric pictures, characterised by a short period of incubation and by a predominance of intestinal symptoms rather than systemic to severe systemic pictures, characterised by septicemia, fever, and even with abortion. Epidemiological analyses highlight that *Salmonella* infections are mainly prevalent in poultry and pigs and, in this context the use of vaccines could be the best instrument to contain infection, wherein it is not possible to reduce the infection incidence by eliminating infected heads.

At the moment, the authorized vaccines for salmonellosis were prepared with inactivated or attenuated bacteria, but effectiveness of such vaccines was very limited. Several approaches to obtain *Salmonella* spp attenuated strains [Cardenas et al., Clin Microbial Rev. 5:328-342 (1992); Chatfield et al., Vaccine 7:495-498 (1989)] were used. These approaches include temperature sensitive mutants [Germanier et al., Infect Immun. 4:663-673 (1971)], mutants defective for biochemical factors (-aroA, -asd, -cys, or -thy [Galan et al., Gene 94:29-35 (1990); Hoiseth et al., Nature 291:238-239 (1981); Robertsson et al., Infect Immun. 41:742-750 (1983)], Δpur and Δdap [Clarke et al., J Vet Res. 51:32-38 (1987); McFarland et al., Microb Pathog. 3:129-141 (1987)]), carbohydrates synthesis defective strains (ΔgalE [Germanier et al., Infect Immun. 4:663-673 (1971); Hone et al., J Infect Dis. 156:167-174 (1987)]), lipopolysaccharide synthesis defective strains (e.g., galE, pmi, rfa), strains lacking plasmids and mutants lacking virulence genes (e.g., invA). However, the effectiveness of these approaches is doubtful and currently is not available the optimum vaccine able to confer long term resistance against *Salmonella* infections.

Available vaccines against salmonellosis may be divided into three categories: (i) vaccines constituted by inactivated bacteria; (ii) vaccines constituted by specific bacterial components (cellular fractions, purified antigens or synthesis analogs); (iii) vaccines constituted by attenuated bacterial strains. Generally speaking, it is broadly accepted that vaccines constituted by attenuated strains are more effective to confer protection because they are still able to induce an infection and to rise an immune response against infection which occurs naturally, but they are not able to damage the host.

In general, all the aforementioned approaches showed a variable effectiveness grade when assayed and the use as vaccine of these attenuated strains showed several limitations, connected to their poor immunogenicity and thus protective capability, to their ability to re-acquire virulent factors, to the presence of genetic factor which confer antibiotic resistance.

Therefore, there is a need of new and more effective tools for the vaccination in veterinary field against *Salmonella* able to reduce the incidence of such infection in animals and overcoming the limitations of vaccines nowadays employed.

The authors of present invention have now found new attenuated *Salmonella* strains through the inactivation of the high affinity zinc transporter system znuABC that unlike other already known attenuated strains, do not lose their ability to invade host cells and to colonize the spleens of infected animals. These mutants, which in particular maintain the ability to multiply particularly in macrophages, showed a marked reduced pathogenicity in animal infection models and conferred at the same time an high degree of protection against subsequent challenge infection with pathogenic Salmonellae.

A number of investigations have revealed that in environments poor of zinc, the ability of Gram-negative bacteria to survive and multiply is critically dependent on the activation of the high affinity transporter system znuABC [Patzer e Hantke, *Mol. Microbiol.* 28, 1199-1210, (1998)]. This system, homologous to other members of the family of ABC transporters (ATP-binding cassette) is constituted by three proteins: ZnuB is an integral membrane protein, ZnuC is the ATPase component of the transporter, whereas ZnuA is a soluble periplasmic metallochaperone which captures zinc in this cellular compartment and then delivers the metal to the transmembrane component of the transporter.

Several studies showed that inactivation of ZnuA or of the other members of the transporter, dramatically influences the capability of bacteria (*H. influenzae, H. ducreyi, B. abortus, P. multocida, N. gonorrhoeae, S. typhimurium*) to grow in zinc poor media and to survive and multiply within the host [Lu et al, *J Biol. Chem.* 272, 29033-29038 (1997); Lewis et al, *Infect Immun.* 67, 5060-5068 (1999); Chen e Morse, FEMS Microbiology Letters, 202, 67-71 (2001); Campoy et al, *Infection and immunity,* 70, 4721-4725 (2002); Gamido et al, *FEMS Microbiol. Letters,* 221, 31-37 (2003); Kim et al, J Vet Med. Sci. 66, 1059-1063 (2005)]. Preliminary studies carried out by the same authors of the invention confirmed the importance of this transporter system in the virulence of *Salmonella* Typhimurium. However, no one of the previous studies hypothesized the possible use for Vaccinal uses of the ZnuABC transporter mutants. These studies suggest that, albeit the high serum or cellular zinc concentration, the amount of free zinc available for microbial growth in host tissues is very limited, as already established for other transition metals. In fact, it is well known that pathogenic bacteria compete with their host for trace elements such as iron and manganese, which are sequestered in forms which limit their reactivity and availability for infectious microorganisms.

Inactivation of the zinc transporter in *Salmonella* strains, through deletion of one of the znuABC operon genes, represents therefore a valid approach to attenuate bacteria without altering their capability to induce an immune based protection against challenge infections with virulent strains. The authors have indeed demonstrated that *Salmonella* Typhimurium ATCC 14028 and Enteritidis LK5 deleted of the znuA gene or of the whole znuABC operon maintain the capability to multiply in macrophages and, at same time, show reduced pathogenicity in Balb/c and DBA2 mice which once immunized with the above mentioned mutants acquire a strong resistance against infection with other virulent strains of the same serotype.

Particularly, these mutants are advantageous because:

1) they confer an high degree of protection towards infections with virulent strains of *Salmonella;*
2) they were obtained by deletion of the gene of interest and it is impossible that they spontaneously revert, reacquiring the original virulence features;
3) this mutation can be easily transduced into all *Salmonella* spp strains susceptible to the P22 phage, through a fast, well standardized and low cost procedure. This can allow a short time production of vaccines still more efficacious through the introduction of this mutation in strains characterized by high diffusion/pathogenicity and in different serotypes. Likewise, the mutation can be easily introduced in other vaccinal strains already in use or under investigation, in order to improve their safety;
4) the strains lack genes conferring resistance to antibiotics or other genetic markers foreign to the microorganism and, it is impossible that the vaccine transfers artificial features to other wild type natural strains;
5) the strains are traceable and distinguishable from wild type *Salmonella* strains by microbiological or molecular biology assays;

Therefore, object of this patent are *Salmonella enterica* attenuated strains, characterized in that they are inactivated at the level of znuABC operon through mutation in at least one of the znuA, znuB, znuC genes of said operon, to be used in medical field, preferably in veterinary field, as vaccines. Such mutation may be effectively introduced at the level of at least one of the znuA, znuB, znuC genes by way of deletion, insertion or substitution. However, gene deletion appears to be the preferable form for vaccine production, as it eliminates reversion risks to the wild type phenotype and environmental diffusion risks of exogenous genetic material which could be potentially dangerous for human and animal health (for example, antibiotic resistance genes). According to a preferred and extensively experimentally embodiment the deletion involves only the znuA gene. According to another embodiment of the invention, also this broadly verified experimentally (see Example 3), all the genes of the znuABC operon are deleted.

Preferably, these *Salmonella enterica* strains are selected between the group of serotypes of medical-veterinary interest, which comprises *Salmonella* Typhimurium, *Salmonella* Enteritidis, *Salmonella* Pullorum, *Salmonella* Typhi, *Salmonella* Abortusovis, *Salmonella* Gallinarum, *Salmonella* Dublin, *Salmonella* Infantis, *Salmonella* Wirchow, *Salmonella* Stanley, *Salmonella* Newport, *Salmonella* Derby, *Salmonella* Hadar, *Salmonella* Choleraesuis, *Salmonella* abortus equi. In a preferred embodiment the *Salmonella* Typhimurium strain is ATCC 14028. According to another preferred embodiment, the *Salmonella* Enteritidis strain is LK5. All the available data suggest that the inactivation of the znuABC operon could be equally effective in all the other strains of *Salmonella enterica.*

In a preferred embodiment the attenuated strains of *Salmonella* mutated at the level of at least one gene of the znuABC operon can be further characterized by a mutation in a second gene responsible of virulence in other already attenuated *Salmonella* strains.

The above described experiments show that mutants lacking a complete ZnuABC zinc uptake system are attenuated and able to confer a high degree of protection towards challenge infection with virulent strains. Therefore, this mutation may be used in association with other defined mutations or introduced in strains attenuated by different ways, in order to improve safety of other *Salmonella* vaccinal strains.

According to an alternative embodiment the attenuated *Salmonella* strains further comprise one or more heterologous antigens. Preferably, said *Salmonella* strain is *Salmonella* Enteritis or Typhimurium, if human beings are the recipients.

In a particularly preferred embodiment of the invention the *Salmonella* strains lack genes able to confer resistance to antibiotics or other genetic markers which are extraneous to the microorganism. The removal may occur through homologous recombination methods which are known to the skilled person in the art and can be appropriate to avoid that the vaccine would transfer artificial features to other bacteria.

It is further object of the present invention the use of the above described attenuated *Salmonella* strains for the preparation of a vaccine to induce an immune response towards *Salmonella* sp., in animal farms or in humans. Such use is useful to reduce the incidence of *Salmonella* contaminations in animal subjected to intensive breeding and, therefore, to favor a reduction of the risk of contamination of foods such as fresh meat, eggs and minced meat products.

Preferably, said animals are selected between aviary species and susceptible mammals (chickens, turkeys, ducks, pigs, ships, bovines, etc.). Using an attenuated *Salmonella* Typhi strain it is possible to set up vaccines for human use able to confer protection against *Salmonella* Typhi.

It is another object of the present invention a vaccine for the prevention of *Salmonella* infection in breeding animals or humans, characterized in that it comprises an attenuated *Salmonella* strain as previously defined, together with carrier and/or excipients pharmacologically acceptable. Preferably, said vaccine comprises between about $10^7$ and about $10^{12}$ CFU (Colony Forming Units), depending on the recipient species.

The invention further concerns the use of the above described attenuated *Salmonella* strains as expression vectors of protective antigens towards infections caused by *Salmonella* or other bacteria which are pathogenic for animals or human beings.

Further object of the present invention is an expression vector of protective antigens against infections caused by *Salmonella* or other pathogenic bacteria, characterized in that it comprises *Salmonella enterica* strains attenuated as above described and further comprising one or more heterologous antigens or molecules with a therapeutic activity. Preferably, said *Salmonella* strain is *Salmonella* Enteritis or Typhimurium, if the recipient are humans. In fact, the strains attenuated through the deletion of a part or of the whole znuABC operon may be advantageously used as expression vectors for protective antigens, preferably heterologous antigens, as these strains maintain the ability to penetrate and multiply in cells of the immune system.

The present invention further relates to a method for the preparation of attenuated *Salmonella enterica* strains comprising the following step:

a) production of one or more inactivating mutations in at least one of the znuA, znuB, znuC genes belonging to znuABC operon by PCR amplification of an antibiotic resistance gene with oligonucleotides having a complementary sequence to the gene to be inactivated, followed by homologous recombination;

b) transduction of the mutation obtained in step a) into a *Salmonella* sppstrain susceptible to phage P22.

Said mutation can be effectively introduced at level of at least one of the znuA, znuB, znuC genes by deletion, insertion or substitution, but preferably by deletion. In a preferred embodiment the mutation is a deletion of the znuA gene. According to an alternative embodiment the mutation involves the whole znuABC operon.

According to a preferred embodiment, said *Salmonella enterica* strains are selected from the group of serotypes consisting in *Salmonella* Typhimurium, *Salmonella* Enteritidis, *Salmonella* Pullorum, *Salmonella* Typhi, *Salmonella* Abortusovis, *Salmonella* Gallinarum. The phage P22 susceptible *Salmonella* sp strains of step b) may also be strains of vaccinal interest already in use or strains where a gene encoding for a n heterologous protective antigen was previously introduced. Preferably, said strains belong to *Salmonella enterica*, and are selected between *Salmonella* Typhimurium, *Salmonella* Enteritidis, *Salmonella* Pullorum, *Salmonella* Typhi, *Salmonella* Abortusovis, *Salmonella* Gallinarum, *Salmonella* Dublin, *Salmonella* Infantis, *Salmonella* Wirchow, *Salmonella* Stanley, *Salmonella* Newport, *Salmonella* Derby, *Salmonella* Hadar, *Salmonella* Choleraesuis, *Salmonella* abortus equi. In a preferred embodiment the strain of *Salmonella* Typhimurium is ATCC 14028. According to another preferred embodiment the strain of *Salmonella* Enteritidis is LK5.

According to a particularly useful embodiment of the present invention, said method comprises a further step c) of elimination of antibiotic resistance genes by induction of homologous recombination. Preferably, this recombination is mediated by a yeast recombinase.

Although the mutation introduced during step a), that is a deletion accompanied by the insertion of an antibiotic resistance gene, is suitable to obtain an effective vaccine, the removal of the resistance gene described in step c) is preferable to improve the safety of the vaccine. For this reason, even if it is possible to obtain mutation of the znuA, znuB, znuC genes also by insertion or substitution, the above mentioned mutation is preferably a deletion.

The present invention now will be described by illustrative but not limitative way according to preferred embodiment thereof with particular reference to the enclosed drawings, wherein:

FIG. 1, shows growth curves of S. Typhimurium 14028 and of a znuA mutant in LB (panel A) and in minimal medium (panel B);

FIG. 2 shows znuA expression in S. Typhimurium: Panel A shows the expression of the znuA protein in LB (lane 1), in LB supplemented with 5 µM (lane 2) and 10 µM (lane 3) $ZnSO_4$ and in LB supplemented with 200 µM (lane 4), 400 µM (lane 5), 600 µM (lane 6), 800 µM (lane 7), 1000 µM (lane 8) e 1500 µM (lane 9) EDTA, respectively; Panel B shows the expression in minimal medium of ZnuA protein analyzed in MM (lane 1) and in MM supplemented with 1 µM (lane 2), 0.5 µM (lane 3), 0.1 µM (lane 4), 0.05 µM (lane 5), 0.01 µM (lane 6) $ZnSO_4$ and in MM supplemented with 5 µM (lane 7), 10 µM (lane 8) e 15 µM (lane 9) EDTA, respectively;

FIG. 3 shows the comparison between the intracellular growth of the *Salmonella* SA123 znuA mutant (squares, dotted line) and wild type S. Typhimurium (triangles, continuous line) in differentiated human monocytes THP-1 (panels A e B) and in colon epithelial cells Caco-2 (panel C); prior to the infection bacteria were cultivated in LB medium (panels A e C) or in LB supplemented with EDTA 1 mM (panel B); the reported cfu/ml values are the average±SD of at least three independent experiments;

FIG. 4 shows the intracellular accumulation of ZnuA in *salmonella*; Panel A shows ZnuA accumulation in bacteria cultivated in a rich medium (LB) and under zinc-limiting conditions (MM), compared to ZnuA accumulation in bacteria extracted from infected macrophages (J774), differentiated monocytes (THP-1) and colonic epithelial cells (Caco-2); each gel shows the results from two independent experiments; Panel B shows ZnuA accumulation in bacteria collected from spleens homogenates of Balb/c mice infected with the SA140 strain (znua-3×FLAG cat-3×FLAG), lanes 1 and 2, and with the strain MA7225 (sodCI-3×FLAG, cat-3× FLAG), lanes 3 and 4; each lane shows the epitope-tagged proteins recovered from different mice;

Figure 12:
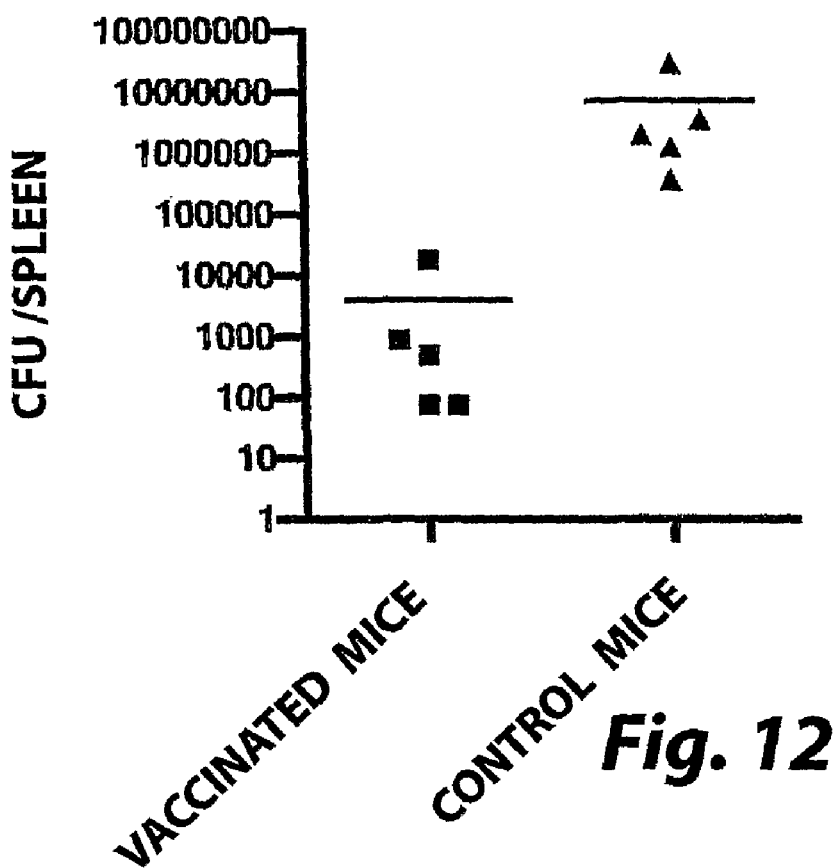
Figure 13:
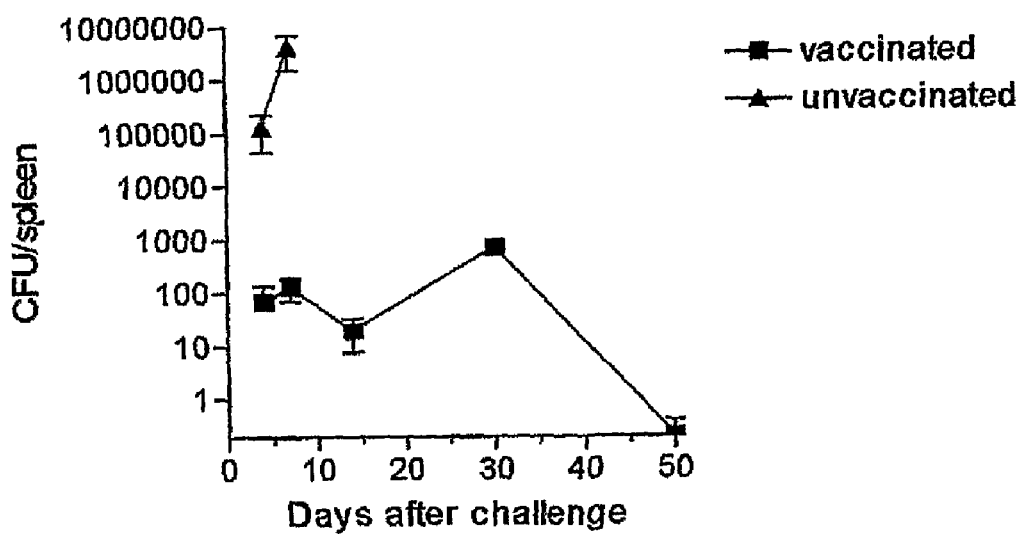

FIG. 12 shows a graph reporting the CFU of bacteria in the spleen of Balb/c mice orally infected with $10^7$ CFU of S. Typhimurium DT104 and sacrificed after 6 days; the figure refers to a group of vaccinated mice ($10^8$ CFU of S. Typhimurium znuA mutant, administered 30 days before by the oral route) and to a group of not treated control mice;

FIG. 13 shows the kinetic of infection in vaccinated and not-vaccinated mice orally infected with the virulent S. Typhimurium 14028 strain.

EXAMPLE 1

Construction of the znuA Gene Deletion Mutants in *Salmonella* Strains Belonging to Serotypes Typhimurium and Enteritidis Bacterial Strains and Plasmid Used

*Salmonella enterica* serotype Typhimurium ATCC 14028 (Fields et al., 1986, Proc. Natl. Acad. Sci. USA 83, 5189-5193) and serotype Enteritidis LK5 (Keller et al, 1993, Avian DiS. 37, 501-507) strains and plasmids pKD46 (Datsenko and Wanner, 2000, Proc Natl Acad Sci USA. 97, 640-645.), pKD4 (Datsenko and Wanner, 2000, Proc Natl Acad Sci USA.

97, 640-645), pCP20 (Datsenko and Wanner, 2000, Proc Natl Acad Sci USA. 97, 640-645.) and pSUB11 (Uzzau et al., 2001, Proc Natl Acad Sci USA. 98, 15264-15269) were provided by Dr. Lionello Bossi (CNRS, Gif-Sur-Yvette, France). S. Typhimurium DT104 strain was provided by Dr. Ida Luzzi (Istituto Superiore si Sanità, Roma, Italy).

Bacteria Culture Media

Bacteria have been cultivated in the rich medium Luria Bertani (LB), or in the Vogel-Bonner minimal medium E (MM)

Cell Lines and Culture Media for Eukaryotic Cells.

Murine macrophages J774 (Balb/C) and TIB-63 (DBA-2) have been supplied by the American Type Culture Collection (ATCC) and cultivated at 37° C. in presence of 5% $CO_2$. The J774 cell line has been cultivated in DMEM containing 4.5 g/L glucose, 2 mM glutamine and 10% fetal bovine serum; the TIB-63 cell line has been cultivated in RPMI 1640 with 2 mM glutamine, 1 mM sodium bicarbonate and 10% foetal bovine serum. Cell culture were supplemented with 1000 U/ml penicillin and 0.1 mg/ml streptomycin. Human colonic epithelial cells were cultivated in DMEM containing 1 g/L glucose, non-essential amino acids, 4 mM glutamine and 10% fetal bovine serum.

Construction of the znuA and znuABC Mutant Strains

To construct deletion mutants in *Salmonella* it has been used a well described method in literature (Wanner e Datsenko, 2000). In particular, to construct the S. Typhimurium znuA::kan mutant, a DNA sequence containing the kanamycin resistance cassette was amplified using plasmid pKD4 as a template for the PCR reaction (Datsenko e Wanner, 2000, Proc Natl Acad Sci USA. 97, 640-645) and the oligonucleotide pair pp 119/pp 120 (SEQ ID NO:3/SEQ ID NO:4) (Table 1).

The oligonucleotides used for the amplification have short homology regions (about 40 bp) with sequences stretches internal to the znuA or znuABC genes (Table 1). The obtained fragment has been subsequently introduced by electroporation in the ATCC14028 strain containing plasmid pKD46 (Datsenko e Wanner, 2000, Proc Natl Acad Sci USA. 97, 640-645) grown at 30° C. in presence of arabinose. Then bacteria have been incubated at 37° C. for an hour, to allow the homologous recombination of the inserted fragment and, at the end of the incubation, they have been plated on LB agar containing kanamycin.

znuA Mutants

The correct insertion of the kanamycin resistance cassette within the znuA gene has been verified by PCR using the oligonucleotides pp 124/kl The oligonucleotide pp 124 (SEQ ID NO:5) pairs with a sequence in proximity of the 5' end of the znuA gene, while the K1 oligonucleotide (SEQ ID NO: 10) pairs with a region within the kanamycin resistance cassette. The mutation thereby produced was subsequently transferred to the wild type strain by P22-mediated generalized transduction. The strain thus obtained was named SA123. By analogy, the mutation has been introduced in *Salmonella enterica* serotype Enteritidis LK5 by P22-mediated generalized transduction.

To eliminate the kanamycin resistance cassette within the znuA gene, the temperature-sensitive plasmid pCP20, bearing a gene coding for the FLP recombinase, has been introduced by electroporation in the SA123 strain. Such recombinase catalyzes the homologous recombination between the two FRT sites which are located at the two ends of the kanamycin resistance cassette. Plasmid pCP20 has been subsequently eliminated by incubation of bacteria at 37° C.

TABLE 1

| Name | Oligonucleotide sequence | Pairing position |
| --- | --- | --- |
| Oli113 (SEQ ID NO: 1) | CCAATTAGCCAACCAGTATGCGAGCT GCCTGAAAGGAGATGACTACAAAGA CCATGACGG | nucleotides 960-999 znuA coding sequence |
| Oli114 (SEQ ID NO: 2) | AATCTCGCTTTTCTCCAGTTCAATAGT TTTAACGATTGGCCATATGAATATCCT CCTTAG | nucleotides 153-192 downstream znuA stop codon |
| Oli119 (SEQ ID NO: 3) | GGAAGCCTTTATGGAGAAGTCGGTC AGGAATATCCCTGATTGTAGGCTGGA GCTGCTTCG | nucleotides 312-351 znuA coding sequence |
| Oli120 (SEQ ID NO: 4) | CGCGCTATCTCTGGGGAGAGCCAAA GATGCATGTTATATTCATATGAATATC CTCCTTAG | nucleotides 485-524 znuA coding sequence |
| Oli124 (SEQ ID NO: 5) | 5'-AAACCACGCGTACAAGCGTT | upstream znuABC |
| Oli128 (SEQ ID NO: 6) | 5'-CCTTTCAGGCAGCTCGCATACTGG TTGGCTAATTGGCTTTGTAGGCTGGA GCTGCTTCG | upstream znuABC |
| Oli130 (SEQ ID NO: 7) | 5'-ATCATACTGAAGATAAACAGCAGC GCGGCACACAGCACTCATATGAATAT CCTCCTTAG | downstream znuABC |
| Oli131 (SEQ ID NO: 8) | 5'-TCATCAGACCTGGGCGATTT | downstream znuABC |
| Oli124 (SEQ ID NO: 9) | AAACCACGCGTACAAGCGTT | nucleotides 172-153 upstream the znuA start codon |

To obtain the znuA::3Xflag ATCC14028 strain, the 3Xflag-kan' from plasmid pSUB11 was amplified by PGR, using the oligonucleotide pair pp 113/pp 114 (SEQ ID NO:1/ SEQ ID NO:2). The pp 113 oligonucleotide pairs at the 3' end of the sequence encoding for the ZnuA protein (excluding the stop codon), whereas the pp 114 oligonucleotide pairs on the opposite strand, in a position downstream the znuA gene. The fragment, purified with Microcon PCR columns, was electroporated in ATCC14028 pKD46 and recombinants were selected on a kanamycin containing medium. To establish that the mutation occurred successfully at the 3' end of the znuA gene, the same procedure described for the isolation of the znuA::kan mutant was used. The znuA::3Xflag [kan'] mutation has been subsequently transferred by generalized transfection in the wild type ATCC14028 strain. To have an internal standard for znuA expression analysis, a chloramphenicol resistance gene (chloramphenicol acetyl transferase, cat) with a 3Xflag fusion at the 3' end was introduced within the ilvH operon, under control of the constitutive tac promoter. The Tn10dTac-caf::3Xflag construct was subsequently transferred by generalized transduction from the strain MA723 7223 (Uzzau, 2001, Proc Natl Acad Sci USA. 98, 15264-15269) into the MA6926 znuA::3Xflag strain. The resulting strain, named SA140, shows, therefore, the following genotype: ilv1H::Tr10dTac-cat::3Xflag znuA::3Xflag. The fusion of the 3Xflag epitope to the znuA gene, as well as the insertion of the cat fusion within the ilv1H operon, did not cause modifications of the growth curves of the two strains compared to the wild type strain.

znuABC Mutants

Apparently, the inactivation of each of the genes of the znuABC operon implies a drastic reduction of S. Typhimurium pathogenicity, with znuA likely playing a major role in comparison to znuC. To obtain the complete removal of the transporter from the vaccinal strain, and, therefore, obtaining a further attenuation of the strain and making still less likely its reversion to a wild type phenotype, we have constructed a strain deleted of the whole znuABC operon. Such mutant exhibits an in vitro phenotype identical to that above described for the znuA mutant.

The construction of the znuABC mutants was carried out by deletion of the whole operon (2786 base pairs) from nucleotide 46 to nucleotide 2503. The deletion was obtained by allelic replacement with a PCR fragment (Datsenko and Wanner, 2000, Proc Natl Acad Sci USA. 97, 640-645) amplified with the oligonucleotides oli-128 (SEQ ID NO:6) and oli-130 (SEQ ID NO:7) using plasmid pkD4 as a template for the reaction. The PCR fragment, which shows short homology regions with sequence stretches within the operon and the kanamycin resistance cassette, was introduced by electroporation in S. Typhimurium ATCC 14028 bearing plasmid pKD46, grown at 30° C. in presence of arabinose. The transformants, selected on LB-kanamycin plates, were tested for their inability to replicate in presence of a divalent metals chelator (EDTA 1 mM); the correct insertion of the kanamycin resistance cassette was verified by PCR using the oligonucleotides couples oli-124 and K1 (SEQ ID NO:5 e SEQ ID NO: 10, which match with some nucleotides upstream znuABC and within the kanamycin resistance cassette, respectively) and oli-124 and oli-131 (SEQ ID NO:5 e SEQ ID NO:8 which match upstream and downstream znuABC, respectively).

The znuABC::kan allele was transferred by phage P22-mediated generalized transduction into the S. Typhimurium ATCC 14028 wild type strain, into S. Enteritidis LK5 and into a S. Enteritidis clinical isolate (IZS#21). The mutants obtained by this procedure were named SA 182 (ATCC 14028 znuABC::kan), SA 196 (LK5 znuABC::kan) and SA 198 (IZS#21 znuABC::kan).

The kanamycin resistance cassette, inserted within the znuABC operon was eliminated by homologous recombination between the FRT sites flanking the cassette, as described in Wanner and Datsenko (2000). Briefly, the pCP20 termosensitive plasmid, which expresses the FLP recombinase and confers ampicilline resistance, was inserted by electroporation in the SA 182, SA 196 e SA 198 strains. Transformants, grown at +30° C., were tested for the loss of kanamycin resistance and subsequently incubated at +37° C. to allow plasmid pCP20 loss (verified on LB plates containing ampicilline). The strains obtained were named SA 186 (14028 ΔznuABC), SA 199 (LK5 ΔznuAB) and SA 202 (IZS#21ΔznuABC).

Infection of Murine Macrophages

For the invasivity and survival experiments of S. Typhimurium strains in eukaryotic cells and to analyze znuA expression in intracellular bacteria stabilized cell lines of murine macrophages (J774 and TIB-63), human monocytes (THP-1), primary murine macrophages taken from peritoneum and human epithelial cells Caco-2 were employed.

Peritoneal cells were collected by a washing procedure carried out with 10 ml of RPMI, using a syringe with a 16 G needle. After cell collection, erythrocytes were eliminated by washing with lysis buffer. Resting macrophages were washed twice with PBS, counted, resuspended in medium and plated. The J774 and TIB-63 lines were cultivated at 37° C. until semi-confluent monolayers were obtained, corresponding to about $2 \times 10^5$ cells/ml. To activate cells, the medium was replaced with a fresh medium without antibiotics and containing 0.1 μg/ml lypopolisaccharide (Sigma; E. coli 055:B5) and cells were incubated at 37° C. for 24 hours. Bacteria, grown in LB or in minimal medium for 18-20 hours, were opsonized with serum prior to the infection by a 30 min incubation at 37° C. The infection was carried out at a multiplicity of infection close to 100 (105 macrophages with 107 bacteria), at 37° C. for 60 minutes. Then, macrophages were washed twice with PBS and medium containing 0.1 mg/ml gentamycin was added. Macrophages were subsequently incubated 1 hour at 37° C. to eliminate extracellular bacteria. At the established times macrophages were lysed with TritonX-100 0.1% (W/V) in cold PBS. Similar procedures were carried out to analyze Salmonella Survival within epithelial Caco-2 cells.

To analyze the intracellular survival of the wild type S. Typhimurium strain (MA 6926) and of the znuA::kan mutant (SA 123) an aliquot of cell lysate was favourably diluted and plated on LB agar to determine the colony forming units (CFU).

To investigate znuA expression, J774, THP-1 and Caco-2 cells lysates were centrifuged and washed once with PBS. The resulting pellet was resuspended in the denaturing solution and boiled 5 min at 100° C. before the electrophoretic separation.

To analyze the expression of znuA in infected animals, Balb/c mice were infected intraperitoneally with approximately 2000 CFU. 4-5 days after the infection animals were sacrificed and the spleens were removed and homogenized. An aliquot of the cellular lysate was properly diluted and plated to count the CFU, while the remaining lysate was centrifuged, resuspended in denaturing solution and boiled for 5 min.

Murine Infections

To evaluate the virulence of the Salmonella strains lacking the znuA gene in comparison with the original bacterial strains, Balb/C and DBA/2 mice, which are considered susceptible and resistant, respectively, to the infection were employed. Groups of at least 5 mice were infected intraperitoneally or orally, with different doses of S. Typhimurium diluted in saline solution, for intraperitoneal inocula, or in sodium bicarbonate (10%) buffer, in case of oral infection. In all cases mice mortality was monitored daily.

To evaluate the ability of the znuA gene deletion mutant to induce an immuno-mediated protection towards infections with lethal doses of *Salmonella* Typhimurium, groups of Balb/c mice were orally immunized with different doses of *Salmonella* Typhimurium lacking znuA gene, diluted in sodium bicarbonate (10%) buffer. A group of mice was inserted in the experimental protocol as non-immunized control group.

Thirty days after the oral administration of the znuA gene deleted *Salmonella* Typhimurium, both the immunized animals and control groups were infected with a lethal dose of *Salmonella* Typhimurium DT104.

Five animals per group were killed 6 days after the infection to evaluate bacterial colonization at the systemic level. The other animals were left alive to monitor mortality over a 3 weeks period.

Results

Phenotypic Characterization of the znuA Mutant In Vitro

Figure 1:
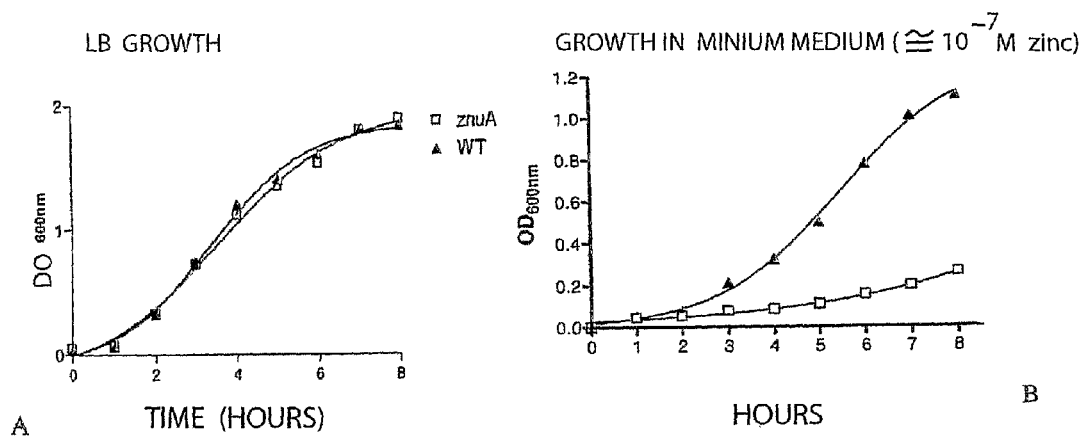

Growth of znuA mutant strains of S. Typhimurium and S. Enteritidis was compared to that of the parental strains under different conditions. The two strains display the same ability to grow in LB medium, likely because of the high zinc concentration present in this medium (FIG. 1, Table 2). However, the addition to the medium of EDTA at a concentration above 0.2 mM inhibits the growth of the wild type mutant, without significantly altering the growth of the wild type strain (Table 2 and data not shown). The ability to grow in presence of EDTA was restored by the introduction of plasmid pSEZnu-AEc, which promotes the constitutive synthesis of *E. coli* ZnuA. In contrast to what is observed in LB, the growth of the znuA mutant is strongly slowed down in minimal medium, where zinc concentration is approximately equal to $10^{-7}$ M.

TABLE 2

Growth of *Salmonella* on rich medium (LB) plates containing EDTA

| EDTA concentration genotype | S. Typhimurium | | | S. Enteritidis | | |
|---|---|---|---|---|---|---|
| | WT | znuA | znuA (pZnuA) | WT | znuA | znuA (pZnuA) |
| 0 | + | + | + | + | + | + |
| 0.2 mM | + | +/− | + | + | − | + |
| 0.5 mM | + | − | + | + | − | + |
| 1 mM | + | − | + | + | − | + |
| 2 mM | + | − | + | + | − | + |

The mutants lacking the whole znuABC operon display an EDTA sensitivity comparable to that of the mutant lacking only the periplasmic transporter ZnuA (not shown). This result suggests that the inactivation of the single znuA gene is sufficient to block zinc import mediated by the high affinity transporter ZnuABC.

The relevance of ZnuA for the growth in media poor of zinc was further confirmed by competition experiments, where bacteria of the mutant strain and bacteria of the parental strain were co-cultivated in LB or minimal medium. As shown in Table 3, the absence of znuA does not cause a selective disadvantage in LB, but significantly alters bacterial ability to grow in a medium poor of zinc.

Comparable phenotypic features were shown by a S. Enteritidis strain lacking znuA. This result suggests that the bacterial znuA-dependence for growth in media poor of zinc is not a feature restricted to S. Typhimurium ATCC 14028, but shared by all the strains belonging to the *Salmonella enterica* genus.

TABLE 3

Competition between the WT and znuA mutant *S. Typhimurium* strains co-cultivatied in LB and minimal medium.

| Culture medium | Number of experiments | Median Competition Index | p |
|---|---|---|---|
| LB | 3 | 1.22 | 0.547 |
| MM | 3 | 0.031 | 0.005* |

*The competition index is obtained from the formula (strain A/strain B) output/(strain A/strain B) input. The statistical analysis of results were carried out with the Student's test; $p < 0.05$ variations were considered significant.

Figure 2:

Parallely, znuA expression was studied in vitro using the SA140 strain, which bears the znuA::3Xflag allele, whose construction was described in Materials and Methods. The results reported in FIG. 2 demonstratethat the znuA gene is completely repressed in bacteria cultivated in LB, but its is induced following the addition of EDTA to the medium or in bacteria cultivated in minimal medium. The addition of zinc at concentrations above 0.1 µM represses znuA expression (FIG. 2, panels A and B).

On the whole, these results confirm and extend what described for the *E. coli* znuA mutants (Patzer, Hantke (1998), *Mol. Microbiol.* 28, 1199-1210) and S. Typhimurium znuC mutant (Campoy et al., 2002, *Infection and immunity,* 70, 4721-4725) and demonstrate that the high affinity zinc transporter ZnuABC is essential for bacterial growth in environments which are poor of this essential element.

Virulence of znuA-Deleted Strain

Figure 9:
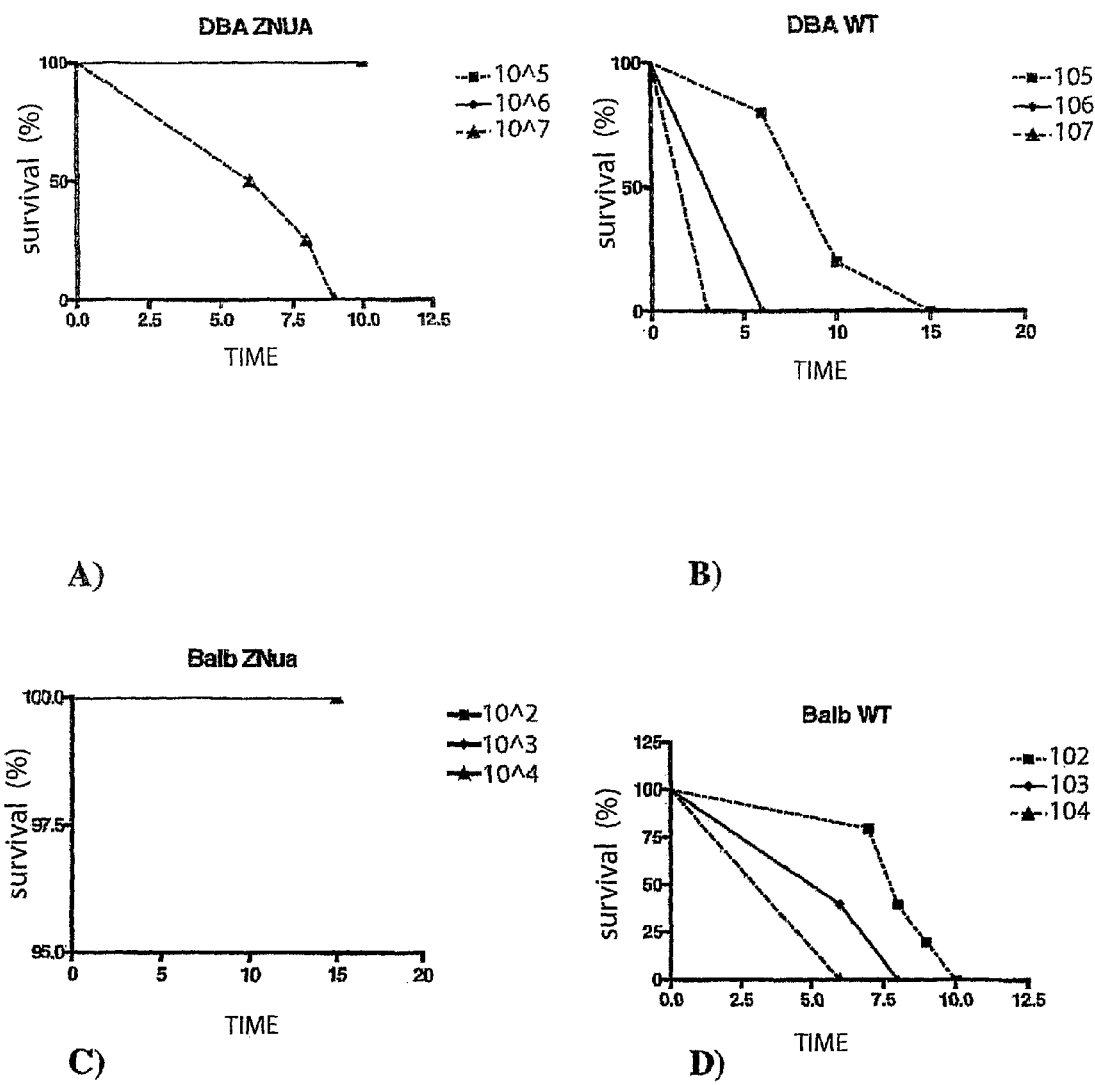
FIG. 9 (Panels A-D) shows the graphs of (%) survival over time of Balb/c and DBA2 mice following the intraperitoneal infection with different doses of Salmonellae (CFU/mice) of S. Enteritidis LK5 ZnuA or wild type.
Figure 10:
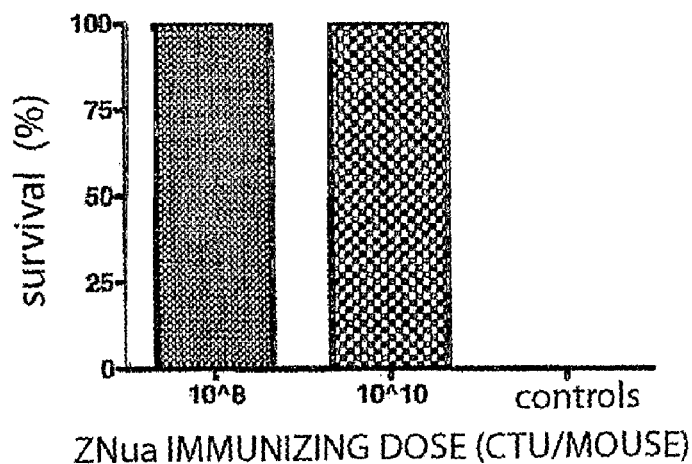
FIG. 10 shows the histogram of the % survival relating to per os immunization of Balb/c mice through different doses of the S. Typhimurium znuA mutant; final oral challenge with a $10^6$ CFU dose of the virulent strain.
Figure 11:
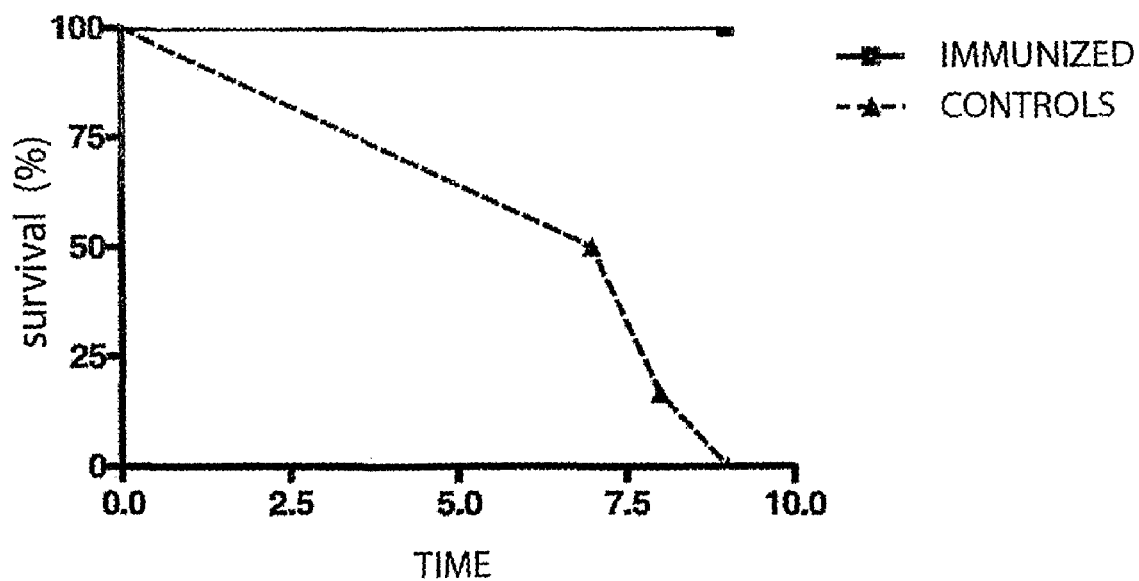
FIG. 11 shows a graph of the % survival relating to immunization obtained by the oral route of Balb/c mice through different doses of the S. Typhimurium znuA mutant; final oral challenge with a $10^7$ CFU dose of the virulent strain.

Virulence has been assessed by using a mouse model of oral or intraperitoneal infection either in Balb/c or in DBA/2 mice (FIGS. 5-8). Survival has been monitored over time. Our results clearly demonstrate that the znuA-deleted S. Typhimurium strain is markedly attenuated in comparison to virulent S. Typhimurium 14028, independently from the route of infection. It is worth observing that the highest doses of *Salmonella* administered through the oral route do not induce mice mortality (the lethal dose is above $10^9$ CFU/mouse). Very similar results were obtained in experiments employing the S. Enteritidis znuA mutant (FIG. 9). In this case, due to a lower pathogenicity of the LK5 strain, *Salmonella* doses required to kill the experimental mice were much higher than those used with S. Typhimurium ATCC14028. These results, all together show that the integrity of the ZnuABC transporter is fundamental for a full virulence of *S. enterica* and suggest that, albeit zinc concentration is apparently elevated in cells and in extracellular environments, during infection bacteria colonize environments where the availability of this metal is limited.

Invasion Efficiency and Intracellular Survival of the znuA Mutant in Cultures.

Figure 3:
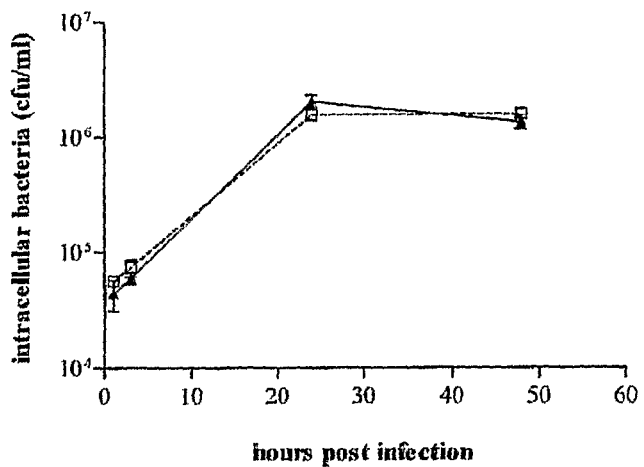
Figure 3:
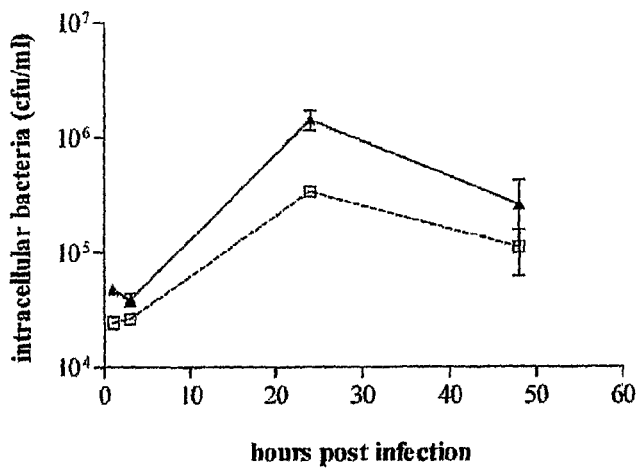
Figure 3:
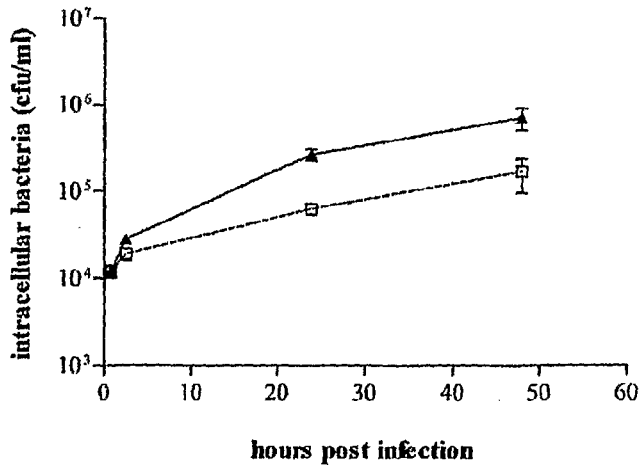

It is known that multiplication of facultative intracellular microorganisms is counteracted by the host thorough iron sequestrations from endosomes, which is mediated by the NRAMP1 protein. In contrast, mechanisms of intracellular zinc compartmentalization in response to microorganisms entry within eukaryotic cells are not known. To verify if the mutation of the znuA gene influences the invasion efficiency and multiplication ability of *Salmonella* within macrophages, we have carried out phagocytosis experiments using cells of the murine lines J774 and TIB-63, human monocyted THP-1 and Caco-2 colonic cells. As it is shown in FIG. 3, the znuA mutation does not significantly influence the penetration or the multiplication of S. Typhimurium within macrophages. In particular, FIG. 3 shows that the deletion of the znuA gene does not modify *Salmonella* entry and survival within human monocycets THP-1 (Panel A). Similar results were obtained with TIB-63 and J774 macrophages. However, the preincubation of bacteria in a zinc-deprived medium (LB+ 1 mM EDTA) significantly decreases *Salmonella* ability to penetrate and survive within these cells (Panel B). A more evident decrease of the multiplication of the znuA mutant was observed in Caco-2 epithelial cells (panel C), also using bacteria precultivated in standard LB.

Similar results were obtained in experiments using peritoneal macrophages isolated from Balb/c and DBA-2 mice. On the contrary, deletion of the znuA gene reduces *Salmonella* ability to multiplicate in epithelial Caco-2 cells. Moreover, we observed that bacteria precultivated in media poor of zinc show a reduced ability to penetrate and multiplicate in the different phagocytes analyzed. This result suggest that, despite the apparent concentration of zinc in all cells is very high, the quota of metal which is effectively available can be limiting for bacterial growth.

Figure 4:
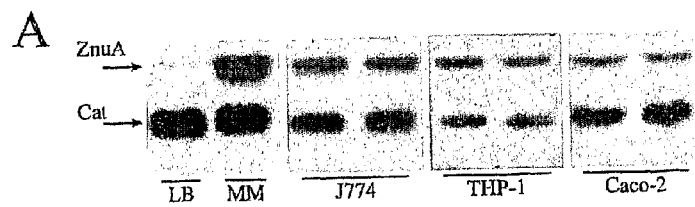
Figure 4:
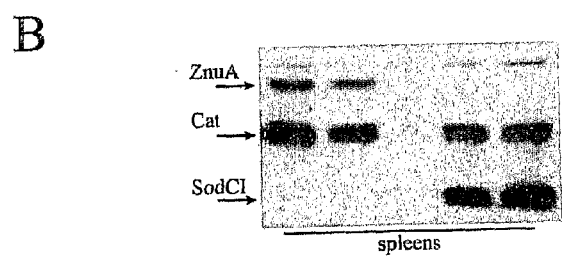
Figure 5:
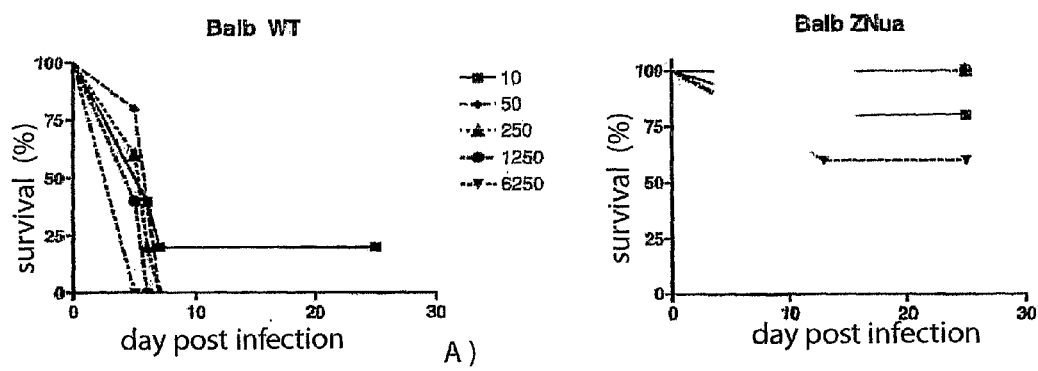
FIG. 5 (panels A and B) shows the graphs of (%) survival over time of Balb/c mice following the intraperitoneal infection with different doses of Salmonellae (CFU/mice) of S. Typhimurium wild type or znuA mutant.
Figure 6:
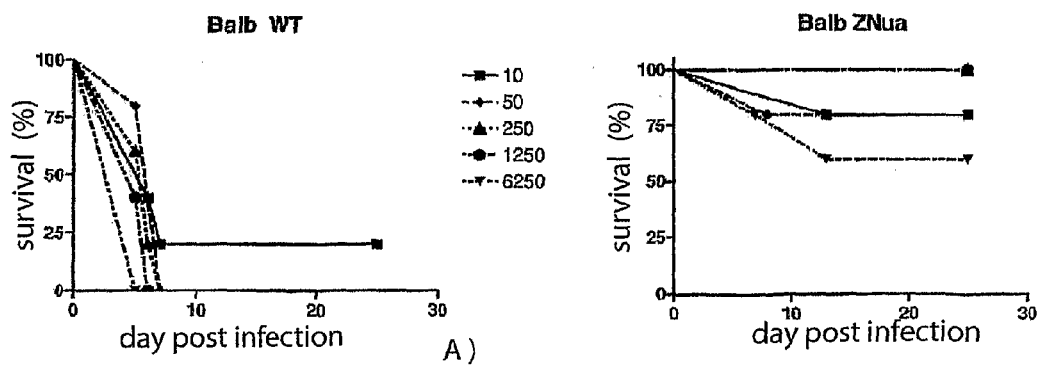
FIG. 6 (panels A and B) shows the graphs of (%) survival over time of Balb/c mice following the oral infection with different doses of Salmonellae (CFU/mice) of S. Typhimurium wild type or znuA mutant.
Figure 7:
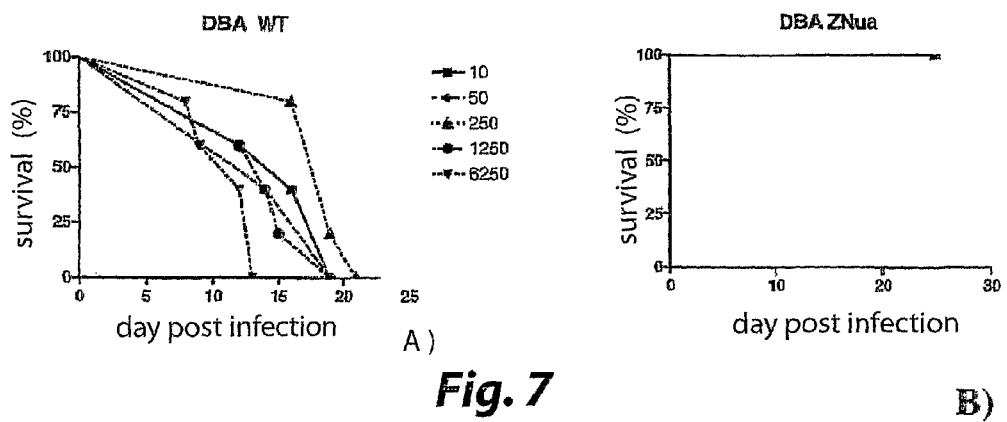
FIG. 7 (panels A and B) shows the graphs of (%) survival over time of DBA2 mice following the intraperitoneal infection with different doses of Salmonellae (CFU/mice) of S. Typhimurium wild type or znuA mutant.
Figure 8:
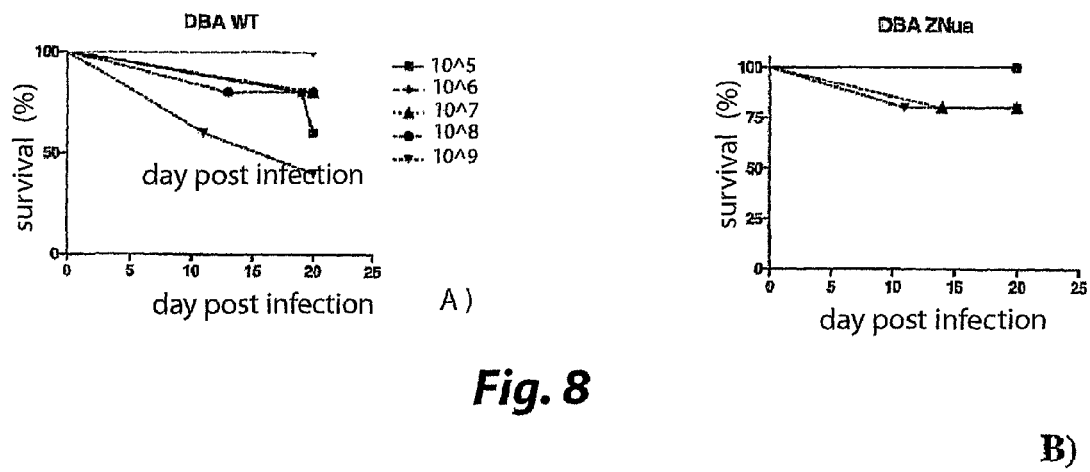
FIG. 8 (panels A and B) shows the graphs of (%) survival over time of DBA2 mice following the oral infection with different doses of Salmonellae (CFU/mice) of S. Typhimurium wild type or znuA mutant.

In confirmation of this hypothesis we observed that ZnuA accumulates at high levels either in the Salmonellae grown in cultured cells or in those recovered from the spleens of intraperitoneally infected Balb-c mice (FIG. 4). In particular, FIG. 4 show ZnuA accumulation in bacteria recovered from J774, THP-1 and Caco-2 cells. ZnuA expression was clearly higher in intracellular bacteria than in bacteria grown in LB. ZnuA appears as highly expressed also in bacteria recovered from the spleens of animals (Balc/c mice) infected with the S. Typhimurium strain SA140. Also in this case, the transporter is clearly induced as well as another virulence factor (SodC1). ZnuA accumulation in intracellular bacteria suggests that these environments are poor of zinc in available forms. Moreover, it is likely that limitation in metal availability might be present also in other districts colonized by the microorganism. In this respect, a number of investigations showed that immediately after microbial invasion a redistribution of zinc within the host organism can be observed (Hill, Poult Sci. 1989, 68, 297-305). In fact, plasmatic zinc concentration notably decreases, whereas a large fraction of zinc is sequestered in the liver, in a form bound to metallothionein. Such response has been usually interpreted as a strategy aimed at increasing zinc availability in the liver, to increase the synthesis of zinc-dependent enzymes potentially useful for the immune response. Our data suggest an alternative hypothesis, that is that zinc decrease in plasma is part of an antimicrobial strategy aimed at the reduction of zinc availability in extracellular compartments. This explanation is compatible with the observation that znuABC is important for full virulence either of facultative intracellular bacteria or of extracellular bacteria (for example, *Haemophilus ducreyi*) able to resist to phagocytosis.

EXAMPLE 2

Demonstration of Vaccinal Effectiveness of znuA-Deleted Attenuated Strains of *Salmonella*

The reduced pathogenicity of *Salmonella* znuA mutants, particularly clear in models of oral infections, suggests that the inactivation of the ZnuABC transporter could be a feasible strategy to obtain alive vaccinal strains to be used against *Salmonella*. However, several avirulent *Salmonella* spp mutants might not be used to this aim, as the lack of virulence is due to inactivation of genes necessary for penetration into host cells and therefore these strains do not guarantee an adequate immune response. In order to evaluate if znuA mutants were able to multiply within hosts, we intraperitoneally administered sublethal doses of S. typhimurium mutant strain into Balb/C mice. Mice were sacrificed 4-5 days after infection and bacterial burden was assessed in spleens. In all the animals high bacterial burden was recovered in spleens ($>10^5$ CFU/spleen), suggesting that the attenuated strain is still able to multiply within the host.

Successively, we performed experiments aiming at the evaluation of the protective efficacy of the administration of sublethal doses of the znuA mutant against virulent strains of S. Typhimurium (FIGS. 10-13). To this aim, Balb/C mice were orally inoculated with znuA deleted S. Typhimurium. A group of mice were kept as control. All the mice were then orally inoculated with lethal doses of wild type S. Typhimurium DT104, one month after vaccination. Five mice per group were then sacrificed 6 days after challenge infection to assess the bacterial burden. The remaining mice were monitored daily to evaluate mortality for a period of 25 days.

Results showed that immunized animals were protected against a challenge infection with at least 100 fold the lethal dose of a S. Typhimurium strain different from the wild type strain ATCC 14028 (data not shown). Interestingly, it is important to highlight that beside its protective effect, the vaccine inoculation is able to markedly reduce the bacterial burden of the wild strain. These findings suggest that mutation of znuA or, more generally, of the znuABC transport system, can be exploited to produce attenuated strains to be used as vaccines. These strains can protect animals against clinical effects of *Salmonella* infection and reduce the presence in organs of infected animals and hence the risk to keep animals as carriers and spreader of Salmonellae. Such mutation could be used alone or in combination with other mutations, in order to increase safety of the vaccine. It is moreover clear that znuA deletion is not strain-specific and it is not limited to *Salmonella* organisms. It therefore suggests that znuABC is the main system exploited by Gram-negative bacteria to acquire zinc in environments poor of this element in a free form.

A study aiming to evaluate the efficacy of znuA-deleted attenuated strains in inducing protection in farm animals against salmonellosis, was then performed. Five chickens of 7 days of age were orally vaccinated with a dose of $10^8$ CFU of S. Typhimurium znuA (123). Five chickens were kept as unvaccinated control animals. Chickens were then infected with $10^9$ UFC of S. Typhimurium DT104, one month after vaccination and killed 6 days after challenge. Spleen, liver and intestine were collected and the presence of Salmonellae was assessed. A microbiological count was performed in spleens and liver, while a qualitative evaluation of the presence of Salmonellae was performed in all the specimens collected. Such qualitative approach does not give us an estimation of the burden of the infection but represent the highest sensibility to assess the presence of the bacteria in hosts.

Gut colonization of wild strain of S. Typhimurium was present in either vaccinated or unvaccinated chickens, 6 days after infection. Internal organs resulted negative in vaccinated chickens while they resulted qualitatively positive in all the unvaccinated chickens. Three out 6 resulted positive to the quantitative assessment showing an infection of moderate entity.

Those results let us to state that znuA deleted attenuated strain of S. Typhimurium, when administered by oral route to chickens of 7 days of age, is able to reduce the subsequent colonization of wild strains and shows its characteristics as potential vaccine stain.

EXAMPLE 3

Study Aiming to Assess Activity of znuABC Deleted Strains

It has been ascertained that znuABC mutants keep capability to induce a immune based protection against virulent S. Typhimurium 14028.

In order to evaluate if the deletion of the entire operon (znuABC) yield a mutant strain which still retains the same capability of znuA deletion mutant to give protection in mice in response to a challenge infection due to S. Typhimurium, 15 DBA mice were vaccinated by an oral delivery of $10^8$ CFU znuABC deletion mutant of S. Typhimurium, and 15 DBA mice were kept as unvaccinated control mice. One month after treatment 5 vaccinated and mice were orally challenged with $10^8$, $10^9$ or $10^{10}$ CFU of virulent S. Typhimurium 14028 and mortality was monitored daily. Vaccinated mice did not show any mortality irrespective to the challenge infection, while unvaccinated mice showed a high degree of mortality (Table 4).

TABLE 4

Survival of vaccinated and unvaccinated mice challenged with different doses of virulent *S. Typhimurium* 14028

| Challenge dose (oral) | vaccinated | unvaccinated |
|---|---|---|
| $10^8$ | 5/5 | 1/5 |
| $10^9$ | 5/5 | 0/5 |
| $10^{10}$ | 5/5 | 0/5 |

Furthermore it was evaluated the ability of vaccinated mice to control the development of an infection induced by a virulent strain.

In order to evaluate the persistence of virulent S. Typhimurium in vaccinated and unvaccinated mice a study of the kinetic of infection was carried out. Twenty DBA were vaccinated orally with an oral delivery of $10^8$ CFU znuABC deletion mutant of S. Typhimurium, and 20 DBA mice were kept as unvaccinated control mice. One month after vaccination, all mice were orally challenged with $3\times10^9$ CFU of virulent S. Typhimurium 14028. Five vaccinated mice were killed at 4, 7, 14, 30 and 50 days after infection. Five unvaccinated mice were killed at 4, and 7 days after infection, the remaining died between 9 and 12 days after challenge. Infection was evaluated by means of the number of bacteria colonizing spleen and by the presence of bacteria in ilea. As depicted in FIG. 13 and Table 5, unvaccinated mice showed higher degree of infection following challenge with virulent S. Typhimurium 14028 in spleen in comparison to vaccinated mice, either at 4 and 7 days after infection. Vaccinated mice showed a very low level of infection throughout the observation with an almost complete clearance at 50 days after challenge infection.

TABLE 5

Presence (positive animals/tested animals) of virulent *S. Typhimurium* 14028 in ilea of unvaccinated and vaccinated mice sacrificed at different time after challenge infection.

| Days after challenge | Vaccinated | Unvaccinated |
|---|---|---|
| 4 | 5/5 | 5/5 |
| 30 | 1/5 | nd* |
| 50 | 0/5 | nd* |

*not done because mice were dead

All together these results showed that znuABC deleted mutant retains the capability to induce a solid, durable and effective immune response against virulent strains.

Finally, it was evaluated if deletion mutants ZnuABC would maintain a long-term ability to induce a protection in response to the infection with virulent strain S-Typhimurium 14028,i.e. 3 months after vaccination.

In order to evaluate the duration of immune based protection induced by vaccination with znuABC deletion mutant of S. Typhimurium, 6 DBA were vaccinated orally with an oral delivery of $10^8$ CFU znuABC deletion mutant of S. Typhimurium, and 6 DBA mice were kept as unvaccinated control mice. Three months after vaccination, all mice were orally challenged with $3\times10^9$ CFU of virulent S. Typhimurium 14028 Vaccinated mice did not show to be susceptible to virulent *Salmonella* infection being alive after a challenge infection. On the contrary, unvaccinated mice within 18 days after challenge infection (data not shown).

The invention claimed is:

1. An immunogenic composition comprising an immunologically effective amount of an attenuated *Salmonella enterica* strain comprising a znuABC operon that has been rendered inoperative by the deletion of the znuA gene of said operon, or by deletion of the entire znuABC operon, and a pharmaceutically acceptable carrier or excipient.

2. The immunogenic composition of claim 1, wherein said *Salmonella enterica* attenuated strain is selected from the group of serotypes consisting of *Salmonella* Typhimurium, *Salmonella* Enteritidis, *Salmonella* Pullorum, *Salmonella* Typhi, *Salmonella* Abortusovis, *Salmonella* Gallinarum, *Salmonella* Dublin, *Salmonella* Infantis, *Salmonella* Wirchow, *Salmonella* Stanley, *Salmonella* Newport, *Salmonella* Derby, *Salmonella* Hadar, *Salmonella* Choleraesuis, and *Salmonella* abortus equi.

3. The immunogenic composition of claim 2, wherein *Salmonella* Typhimurium strain is *Salmonella* Typhimurium ATCC 14028.

4. The immunogenic composition of claim 2, wherein *Salmonella* Enteritidis strain is LK5.

5. The vaccine immunogenic composition of claim 1, further comprising a mutation in a second gene responsible for virulence in *Salmonella* strains.

6. The immunogenic composition of claim 1, further comprising one or more heterlogous antigens.

7. The immunogenic composition of claim 6, which is Enteritis or Typhimurium for a human recipient.

8. The immunogenic composition of claim 1, lacking genes able to confer antibiotic resistance or another genetic marker exogenous to the microorganism.

9. The immunogenic composition of claim 1, which induces an immune response against *Salmonella* sp. in breeding animals or in humans.

10. The immunogenic composition of claim 1, wherein said *Salmonella enterica* strain is *Salmonella* Enteritidis or Typhimurium.

11. The immunogenic composition of claim 1, wherein said strain is *Salmonella* Typhi and induces an immune response against *Salmonella* Typhi in humans.

12. The immunogenic composition of claim 1, wherein the attenuated *Salmonella enterica* strain is selected from the group consisting of *Salmonella* Gallinarum, *Salmonella* Choleraesuis, *Salmonella* Abortusovis, *Salmonella* abortus equi for use in poultry, pigs, sheep, and equines, respectively.

13. The immunogenic composition of claim 1, wherein *Salmonella* infection is reduced in animals that were administered the immunogenic composition as compared to the *Salmonella* infection in animals that were not administered the immunogenic composition, where the animals are selected from the group consisting of poultry and mammals.

14. The immunogenic composition of claim 1, comprising between approximately $10^7$ and $10^{12}$ CFU of bacteria.

15. The immunogenic composition of claim 13, wherein said animals are selected from the group consisting of chickens, turkeys, ducks, pigs, sheep and cows.

* * * * *

```
                          SEQUENCE LISTING

<160> NUMBER OF SEQ ID NOS: 10

<210> SEQ ID NO 1
<211> LENGTH: 60
<212> TYPE: DNA
<213> ORGANISM: Artificial
<220> FEATURE:
<223> OTHER INFORMATION: Primer mapping nucleotides 960-999 of the znuA
      encoding sequence

<400> SEQUENCE: 1
ccaattagcc aaccagtatg cgagctgcct gaaaggagat gactacaaag accatgacgg     60

<210> SEQ ID NO 2
<211> LENGTH: 60
<212> TYPE: DNA
<213> ORGANISM: Artificial
```

```
<220> FEATURE:
<223> OTHER INFORMATION: Primer mapping nucleotides 153-192 downstream
      the stop codon of znuA

<400> SEQUENCE: 2
aatctcgctt ttctccagtt caatagtttt aacgattggc catatgaata tcctccttag    60

<210> SEQ ID NO 3
<211> LENGTH: 60
<212> TYPE: DNA
<213> ORGANISM: Artificial
<220> FEATURE:
<223> OTHER INFORMATION: Primer mapping nucleotides 312-351 of the
      sequence encoding znuA

<400> SEQUENCE: 3
ggaagccttt atggagaagt cggtcaggaa tatccctgat tgtaggctgg agctgcttcg    60

<210> SEQ ID NO 4
<211> LENGTH: 60
<212> TYPE: DNA
<213> ORGANISM: Artificial
<220> FEATURE:
<223> OTHER INFORMATION: Primer mapping nucleotides 485-524 of the
      sequence encoding znuA

<400> SEQUENCE: 4
cgcgctatct ctggggagag ccaaagatgc atgttatatt catatgaata tcctccttag    60

<210> SEQ ID NO 5
<211> LENGTH: 20
<212> TYPE: DNA
<213> ORGANISM: Artificial
<220> FEATURE:
<223> OTHER INFORMATION: Primer mapping upstream znuABC

<400> SEQUENCE: 5
aaaccacgcg tacaagcgtt                                                20

<210> SEQ ID NO 6
<211> LENGTH: 60
<212> TYPE: DNA
<213> ORGANISM: Artificial
<220> FEATURE:
<223> OTHER INFORMATION: Primer mapping upstream znuABC

<400> SEQUENCE: 6
tcctttcagg cagctcgcat actggttggc taattggctt tgtaggctgg agctgcttcg    60

<210> SEQ ID NO 7
<211> LENGTH: 60
<212> TYPE: DNA
<213> ORGANISM: Artificial
<220> FEATURE:
<223> OTHER INFORMATION: Primer mapping downstream znuABC

<400> SEQUENCE: 7
catcatactg aagataaaca gcagcgcggc acacagcact catatgaata tcctccttag    60

<210> SEQ ID NO 8
<211> LENGTH: 20
<212> TYPE: DNA
<213> ORGANISM: Artificial
<220> FEATURE:
<223> OTHER INFORMATION: Primer mapping downstream znuABC

<400> SEQUENCE: 8
```

-continued

```
tcatcagacc tgggcgattt                                              20

<210> SEQ ID NO 9
<211> LENGTH: 20
<212> TYPE: DNA
<213> ORGANISM: Artificial
<220> FEATURE:
<223> OTHER INFORMATION: Primer mapping nucleotides 172-153 upstream
      start codon of znuA

<400> SEQUENCE: 9
aaaccacgcg tacaagcgtt                                              20

<210> SEQ ID NO 10
<211> LENGTH: 20
<212> TYPE: DNA
<213> ORGANISM: Artificial
<220> FEATURE:
<223> OTHER INFORMATION: Primer mapping the inner region of the cassette
      of kanamicine resistance

<400> SEQUENCE: 10
cagtcatagc cgaatagcct                                              20
```